(12) United States Patent
Russell et al.

(10) Patent No.: US 11,752,489 B2
(45) Date of Patent: Sep. 12, 2023

(54) AFFINITY DISSOLUTION OF BIOMOLECULES FOR PROTEIN PURIFICATION

(71) Applicant: Biohybrid Solutions LLC, Pittsburgh, PA (US)

(72) Inventors: Alan Russell, Wexford, PA (US); Marina Kovaliov, Pittsburgh, PA (US); Amanda Fisher, Cheswick, PA (US)

(73) Assignee: BIOHYBRID SOLUTIONS LLC, Pittsburgh, PA (US)

( * ) Notice: Subject to any disclaimer, the term of this patent is extended or adjusted under 35 U.S.C. 154(b) by 127 days.

(21) Appl. No.: 16/949,170

(22) Filed: Oct. 16, 2020

(65) Prior Publication Data

US 2022/0134309 A1    May 5, 2022

Related U.S. Application Data

(60) Provisional application No. 62/915,673, filed on Oct. 16, 2019.

(51) Int. Cl.
*C07K 16/00* (2006.01)
*B01J 20/26* (2006.01)
*C07K 1/22* (2006.01)

(52) U.S. Cl.
CPC ............ *B01J 20/261* (2013.01); *C07K 1/22* (2013.01); *C07K 16/00* (2013.01)

(58) Field of Classification Search
CPC . C07K 1/32; C07K 1/145; C07K 1/30; C07K 17/08
See application file for complete search history.

(56) References Cited

U.S. PATENT DOCUMENTS

| | | | |
|---|---|---|---|
| 2010/0099160 A1* | 4/2010 | Jiang | G01N 33/545 527/300 |
| 2011/0294189 A1* | 12/2011 | Chilkoti | C07K 1/1075 530/402 |
| 2017/0253673 A1* | 9/2017 | Kent | C09D 101/12 |

FOREIGN PATENT DOCUMENTS

JP        H09327288       * 12/1997

OTHER PUBLICATIONS

Translation of JPH09327288 (Year: 1997).*

* cited by examiner

*Primary Examiner* — Robert C Boyle
(74) *Attorney, Agent, or Firm* — Procopio, Cory, Hargreaves & Savitch LLP (57) ABSTRACT

Protein-based affinity ligands, in which the protein has an affinity for a target protein and includes a covalently attached polyelectrolyte, and methods for using the same to purify proteins are described herein.

16 Claims, 8 Drawing Sheets

AFFINITY DISSOLUTION OF BIOMOLECULES FOR PROTEIN PURIFICATION

CROSS-REFERENCE TO RELATED APPLICATIONS

This application claims priority from U.S. Provisional No. 62/915,673 entitled "Affinity Dissolution of Biomolecules for Protein Purification," filed Oct. 16, 2019, the contents of which are hereby incorporated by reference in its entirety.

GOVERNMENT INTERESTS

Parties to a Joint Research Agreement

Not applicable

Incorporation of Material on Compact Disc

Not applicable

BACKGROUND

Proteins are not soluble in saturated solutions of salts (including ammonium sulfate). As a result, ammonium sulfate has frequently been used to precipitate proteins as a general class from cell extracts and complex mixtures as a low-resolution purification step. High resolution protein purification is typically performed using chromatographic processes in which proteins are transferred from solution to a solid support phase during flow and then released when desired. Specific interactions between the solid support and a single protein, or class of proteins, can be particularly useful. Affinity chromatography is particularly attractive for this purpose. Affinity ligands have also been used for decades to induce precipitation of specific proteins from complex mixtures.

Affinity precipitation, in which a specific ligand binding interaction causes a protein to specifically fall out of solution, has been pursued for over fifty years as an alternative to large scale affinity-based purification. Unfortunately, affinity precipitation does not provide complete phase separation, does not have sharp transitions, forms large precipitates that can trap impurities, and has limited yield. An affinity ligand that keeps a specific biomolecule in solution at high salt concentrations could be transformational since all other proteins are neither soluble nor active under those conditions. However, as stated above, all proteins are insoluble in saturated ammonium sulfate solutions.

SUMMARY OF THE INVENTION

Various embodiments of the invention are directed to protein-based affinity ligands including a protein and a covalently attached to a betaine osmolyte. In some embodiments, the protein may be various antibodies, protein A, protein G, protein A/G, protein L, jacalin, and the like, and the betaine osmolyte may be sulfobetaine methacrylate (SBMA), sulfobetaine acrylate, sulfobetaine acrylamide, sulfobetaine methacrylamide, carboxybetaine methacrylate (CBMA), carboxybetaine acrylate, carboxybetaine acrylamide, carboxybetaine methacrylamide, phosphorylcholine methacrylate (PCMA), phosphorylcholine acrylate, phosphorylcholine acrylamide, phosphorylcholine methacrylamide, and the like and combinations thereof. In particular embodiments, the betaine osmolyte may be poly(carboxy betaine methacrylate) (polyCBMA), poly(carboxybetaine acrylate), poly(carboxybetaine acrylamide), poly(carboxybetaine methacrylamide), poly(sulfobetaine methacrylate) (poly SBMA), poly(sulfobetaine acrylate), poly(sulfobetaine acrylamide), poly(sulfobetaine methacrylamide), poly(phosphorylcholine methacrylate) (polyPCMA), poly(phosphorylcholine acrylate), poly(phosphorylcholine acrylamide), poly(phosphorylcholine methacrylamide), and the like.

Other embodiments are directed to methods for purifying proteins including the steps of adding a protein-based affinity ligand including a protein and a covalently attached to a betaine osmolyte to a solution containing a target protein, adding a precipitant to the solution, recovering the supernatant, and extracting the target protein from the protein-based affinity ligand. In some embodiments, the method may include removing the precipitated proteins from the solution. The precipitant of various embodiments may be chloride salts, sulfate salts, phosphate salts, acetate salts, citrate salts, sodium chloride, ammonium sulfate, ammonium chloride, potassium chloride, sodium acetate, and the like and combinations thereof, and in certain embodiments, the precipitant imay be a salt solution having saturation level of greater than about 40%. In some embodiments, extracting the target protein may include decreasing the pH of the solution containing the protein-based affinity ligand-target protein complexes, and in particular embodiments, the pH of the solution may be lowered to a pH of about 5 to about 3.

In some embodiments, the protein of the protein-based affinity ligand used in such methods may be various antibodies, protein A, protein G, protein A/G, protein L, jacalin, and the like, and the betaine osmolyte of the protein-based affinity ligand may be sulfobetaine methacrylate (SBMA), sulfobetaine acrylate, sulfobetaine acrylamide, sulfobetaine methacrylamide, carboxybetaine methacrylate (CBMA), carboxybetaine acrylate, carboxybetaine acrylamide, carboxybetaine methacrylamide, phosphorylcholine methacrylate (PCMA), phosphorylcholine acrylate, phosphorylcholine acrylamide, phosphorylcholine methacrylamide, and the like and combinations thereof. In particular embodiments, the betaine osmolyte protein-based affinity ligand used in the methods of embodiments may be poly(carboxy betaine methacrylate) (polyCBMA), poly(carboxybetaine acrylate), poly(carboxybetaine acrylamide), poly(carboxybetaine methacrylamide), poly(sulfobetaine methacrylate) (poly SBMA), poly(sulfobetaine acrylate), poly(sulfobetaine acrylamide), poly(sulfobetaine methacrylamide), poly(phosphorylcholine methacrylate) (polyPCMA), poly(phosphorylcholine acrylate), poly(phosphorylcholine acrylamide), poly(phosphorylcholine methacrylamide), and the like.

Further embodiments include methods for purifying a protein including the steps of adding a protein-based affinity ligand comprising a protein and a covalently attached to a betaine osmolyte to a solution containing a target protein, reducing the temperature of the solution, concentrating a precipitated protein-based affinity ligand-target protein complexes from the solution, and removing the supernatant. In some embodiments, the method may include the step of resuspending the precipitated protein-based affinity ligand-target protein complexes in a solution and extracting the target protein from the protein-based affinity ligand. In some embodiments, extracting may include decreasing the pH of the solution containing the protein-based affinity ligand-target protein complexes, and in certain embodiments, the pH of the solution may be lowered to a pH of about 5 to about 3.

In some embodiments, the protein of the protein-based affinity ligand used in such methods may be various antibodies, protein A, protein G, protein A/G, protein L, jacalin, and the like, and the betaine osmolyte of the protein-based affinity ligand may be sulfobetaine methacrylate (SBMA), sulfobetaine acrylate, sulfobetaine acrylamide, sulfobetaine methacrylamide, carboxybetaine methacrylate (CBMA), carboxybetaine acrylate, carboxybetaine acrylamide, carboxybetaine methacrylamide, phosphorylcholine methacrylate (PCMA), phosphorylcholine acrylate, phosphorylcholine acrylamide, phosphorylcholine methacrylamide, and the like and combinations thereof. In particular embodiments, the betaine osmolyte protein-based affinity ligand used in the methods of embodiments may be poly(carboxy betaine methacrylate) (polyCBMA), poly(carboxybetaine acrylate), poly(carboxybetaine acrylamide), poly(carboxybetainemethacrylamide), poly(sulfobetaine methacrylate) (poly SBMA), poly(sulfobetaine acrylate), poly(sulfobetaine acrylamide), poly(sulfobetaine methacrylamide), poly(phosphorylcholine methacrylate) (polyPCMA), poly(phosphorylcholine acrylate), poly(phosphorylcholine acrylamide), poly(phosphorylcholine methacrylamide), and the like.

DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 ml to 8 ml is stated, 2 ml, 3 ml, 4 ml, 5 ml, 6 ml, and 7 ml are also intended to be explicitly disclosed, as well as the range of values greater than or equal to 1 ml and the range of values less than or equal to 8 ml.

All percentages, parts and ratios are based upon the total weight of the topical compositions and all measurements made are at about 25° C., unless otherwise specified.

The singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The term "controlled radical polymerization initiator" refers to a molecule that generates a radical species to begin the synthesis of a polymer chain by successive addition of free-radical building blocks. The terms "controlled radical polymerization initiator" and "initiator" are used interchangeably herein to refer to a molecule that begins a radical polymerization process.

The term "protein-initiator conjugate" refers to a complex that comprises both a protein and one or more controlled radical polymerization initiators, such as five or more, 10 or more, 25 or more, 50 or more, or 100 or more controlled radical polymerization initiators. Preferably, the one or more controlled radical polymerization initiators are covalently attached to the protein. As used herein, a protein-initiator conjugate is a specific type of biomolecule-initiator conjugate, wherein the biomolecule is a protein.

The term "atom transfer radical polymerization" (ATRP) refers to a polymerization technique that forms carbon-carbon bonds via a transition metal catalyst.

The term "salts" as used herein embraces pharmaceutically acceptable salts commonly used to form alkali metal salts of free acids and to form addition salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Non-limiting examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, analogs, compounds, ligands, structures, or groups thereof, or any members of a claimed group, less than the full measure of this disclosure can be claimed for any reason. Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Proteins are not soluble in saturated solutions of salts (including ammonium sulfate). As a result, ammonium sulfate has frequently been used to precipitate proteins as a general class from cell extracts and complex mixtures as a low-resolution purification step. High resolution protein purification is typically performed using chromatographic processes in which proteins are transferred from solution to a solid support phase during flow and then released when desired. Specific interactions between the solid support and a single protein, or class of proteins, can be particularly useful. Affinity chromatography is particularly attractive for this purpose. Affinity ligands have also been used for decades to induce precipitation of specific proteins from complex mixtures.

Affinity precipitation, in which a specific ligand binding interaction causes a protein to specifically fall out of solution, has been pursued for over fifty years as an alternative to large scale affinity-based purification. Unfortunately, affinity precipitation does not provide complete phase separation, does not have sharp transitions, forms large precipitates that can trap impurities and have limited yield. An affinity ligand that keeps a specific biomolecule in solution at high salt concentrations could be transformational since all other proteins are neither soluble nor active under those conditions. However, as stated above, all proteins are insoluble in saturated ammonium sulfate solutions.

Various embodiments include protein-based affinity ligands that are completely soluble at all concentrations of ammonium sulfate. The ligands act as specific carriers that cause bound target proteins to remain soluble in ammonium sulfate when all other proteins precipitate. further embodiments are directed to methods for making the protein-based affinity ligands, and other embodiments include methods for using the protein-based affinity ligands to purify proteins. Unlike affinity precipitation, affinity dissolution offers complete phase separation (only a protein bound to our Affinity Dissolution Carriers remain in solution) and high purification yields. The opportunity to replace chromatography with a simple precipitation of all contaminating proteins is transformational.

The protein-based affinity ligand of such embodiments may include a support protein and a covalently attached polyelectrolyte. In some embodiments, the support protein may be a protein capable of binding to other proteins, antibodies, and enzymes. For example, in particular embodiments, the support protein may be an immunoglobulin-binding protein such as, for example, antibodies, protein A, protein G, protein A/G, protein L, and jacalin.

The covalently attached polyelectrolyte may be any polymer that creates an electrically conducting solution when dissolved in a polar solvent, such as water, thereby increasing the solubility of the support protein in the polar solvent. In some embodiments, the polar solvent may include salts such as, for example, ammonium sulfate, that would otherwise cause the support protein to become insoluble and precipitate out of the solvent/salt containing solution. Protein solubility depends on numerous intrinsic and extrinsic factors. The intrinsic chemical structure of the protein surface and the number of charged amino acids influence solubility. In aqueous solutions, solubility is proportional to the number of charged amino acids on the protein surface. Interestingly, proteins are least soluble at their isoelectric point (pI) where they have no net charge. Extrinsic factors including temperature, pH, ionic strength, and other additives can also impact solubility.

In some embodiments, the polyelectrolyte may be a zwitterionic polymer, and in some embodiments, the polyelectrolyte may contain a betaine osmolyte, such as polymers containing repeating units of sulfobetaine-containing monomer, carboxybetaine-containing monomers, or combinations thereof. Examples of sulfobetaine-containing monomer and carboxybetaine-containing monomers include, but are not limited to, sulfobetaine methacrylate (SBMA), sulfobetaine acrylate, sulfobetaine acrylamide, sulfobetaine methacrylamide, carboxybetaine methacrylate (CBMA), carboxybetaine acrylate, carboxybetaine acrylamide, carboxybetaine methacrylamide, phosphorylcholine methacrylate (PCMA), phosphorylcholine acrylate, phosphorylcholine acrylamide, phosphorylcholine methacrylamide, and the like and combinations thereof. Examples of sulfobetaine and carboxybetaine containing polymers include, but are not limited to, poly(carboxy betaine methacrylate) (polyCBMA), poly(carboxybetaine acrylate), poly(carboxybetaine acrylamide), poly(carboxybetaine methacrylamide), poly(sulfobetaine methacrylate) (poly SBMA), poly(sulfobetaine acrylate), poly(sulfobetaine acrylamide), poly(sulfobetaine methacrylamide), poly(phosphorylcholine methacrylate) (polyPCMA), poly(phosphorylcholine acrylate), poly(phosphorylcholine acrylamide), poly(phosphorylcholine methacrylamide), and the like. Additional embodiments include random and block copolymers of any of the sulfobetaine-containing monomer and carboxybetaine-containing monomers described above and oligomers thereof. In further embodiments, the polymer containing sulfobetaine-containing monomer, carboxybetaine-containing monomers, sulfobetaine-containing oligomers, carboxybetaine-containing oligomers and combinations thereof, and one or more additional monomers non-sulfobetaine-containing or carboxybetaine-containing monomers. The additional monomers can be zwitterionic or non-zwitterionic monomers.

The protein-based affinity ligands of embodiments described above may be soluble in saturated solutions, including, for example, saturated solutions of ammonium sulfate or other salts used for protein precipitation. When protein-based affinity ligands such as those described above are complexed with a target protein, the combined complex may remain soluble in a saturated solution, while all other protein components precipitate in the solution. Through this "come along for the ride" approach we can address all the weaknesses of affinity precipitation, opening the door to a viable, simple, and reproducible alternative to protein-based affinity chromatography.

Thus, embodiments of the invention include methods for purifying proteins including the steps of adding a protein-based affinity ligand, in which the protein of the protein-based affinity ligand can bind to a target protein, to a solution containing a target protein, and adding a precipitant to the solution. The protein in such embodiments may be an immunoglobulin or other protein having an affinity for the target protein. In some embodiments, the method may further include the steps of removing the precipitated proteins from the solution by, for example, centrifugation. The supernatant remaining after removing precipitated proteins may contain the protein-based affinity ligand and target protein bound by the protein of the protein-based affinity ligand. Other embodiments include the steps of recovering the supernatant and extracting the target protein from the protein-based affinity ligand.

In such embodiments, the precipitant may be a salt or salt solution that is added to the solution containing the target protein. Such salts include, but are not limited to, chloride salts, sulfate salts, phosphate salts, acetate salts, citrate salts, sodium chloride, ammonium sulfate, ammonium chloride, potassium chloride, sodium acetate, and the like and combinations thereof. When a salt solution is used, the solution may be saturated, meaning no more of the salt can be dissolved into the solution. In other embodiments, the solution may have a saturation level of greater than about 40%, greater than about 50%, greater than about 60%, greater than about 70%, greater than about 80% or any range or individual value encompassed by these example ranges. In other embodiments, the solution may have a saturation level of about 40% to about 85%, about 50% to about 85%, about 60% to about 85%, about 70% to about 85%, or any range or individual value encompassed by these example ranges.

The target protein containing solution may be centrifuged after the precipitant has been added to concentrate precipitated proteins and the supernatant may be removed. The supernatant of such embodiments may include protein-based affinity ligand-target protein complexes with few, if any, contaminating proteins. The target protein may be extracted from the protein-based affinity ligand to produce a purified target protein.

In some embodiments, methods for purifying proteins can be carried out using upper critical solution temperature (UCST). Such embodiments may include the step of adding a protein-based affinity ligand, in which the protein of the protein-based affinity ligand can bind to a target protein, to a solution containing a target protein, and reducing the temperature of the solution. Reducing the temperature of the solution may cause protein-based affinity ligand-target protein complexes to precipitate from the solution. The method may further include the steps of concentrating the precipitated protein-based affinity ligand-target protein complexes from the solution by, for example, centrifugation, and removing the supernatant. The method may include resuspending the precipitated protein-based affinity ligand-target protein complexes in a solution and extracting the target protein from the protein-based affinity ligand.

The target protein containing solution may be centrifuged after the precipitant has been added to concentrate precipitated proteins and the supernatant may be removed. Pellet created by centrifugation of such embodiments may include protein-based affinity ligand-target protein complexes with few, if any, contaminating proteins. The pellet may then by resuspended and the target protein may be extracted from the protein-based affinity ligand, producing a purified target protein.

Extracting can be carried out by various means including, for example, decreasing the pH of the solution containing the protein-based affinity ligand-target protein complexes. Decreasing the pH of the solution can be carried out by adding an acid or acidifying agent to the solution to reduce the pH to less than about 5, less than about 4, less than about 3, about 5 to about 3, about 4 to about 3, or any range or individual value encompassed by these ranges. The acid or acidifying agent may vary among embodiments and may include hydrochloric acid, acetic acid, citric acid, and the like and solutions containing hydrochloric acid, acetic acid, citric acid, and the like In embodiments in which a precipitant is used, the pH of the supernatant may be decreased causing the target protein to be released from the protein-based affinity ligand, and the target protein may immediately precipitate from the solution when released. The composition created by decreasing the pH may then be centrifuged to concentrate the precipitated protein, the supernatant may be removed, and the pellet may be resuspended to produce a solution containing the purified target protein.

Yet other embodiments include methods for making a protein-based affinity ligand. Any method for grafting a polyelectrolyte onto a protein or causing polymerization of a polyelectrolyte on a protein can be used in such embodiments. In some embodiments, the polyelectrolyte can be grafted onto the protein by atom transfer radical polymerization (ATRP). Such methods may include the introducing a transition metal catalyst into a solution containing a protein and one or more monomers such as the sulfobetaine-containing monomer, carboxybetaine-containing monomers, or combinations thereof described above. In some embodiments, the method may further include introducing an initiator to the solution containing a protein and one or more monomers and a transition metal catalyst.

The transition metal catalyst may contain any transition metal, for example, copper (Cu), iron (Fe), ruthenium (Ru), nickel (Ni), osmium (Os), or combinations thereof, and the initiator may be an alkyl halide. In an ATRP process, a dormant species is activated by the transition metal catalyst generating radicals on the protein surface or on the monomer, while the transition metal is oxidized. This is a reversible process that rapidly establishes an equilibrium. The number of monomers in the polyelectrolyte chain is determined by the concentration of initiator. As a result, polymers with similar molecular weights and narrow molecular weight distribution can be prepared.

ATRP reactions can be carried out with various functional groups like allyl, amino, epoxy, hydroxy, and vinyl groups present in either the monomer or the initiator. ATRP methods are also advantageous due to the ease of preparation, commercially available and inexpensive catalysts, typically, copper complexes, pyridine-based ligands, and alkyl halide initiators.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

Figure 1:
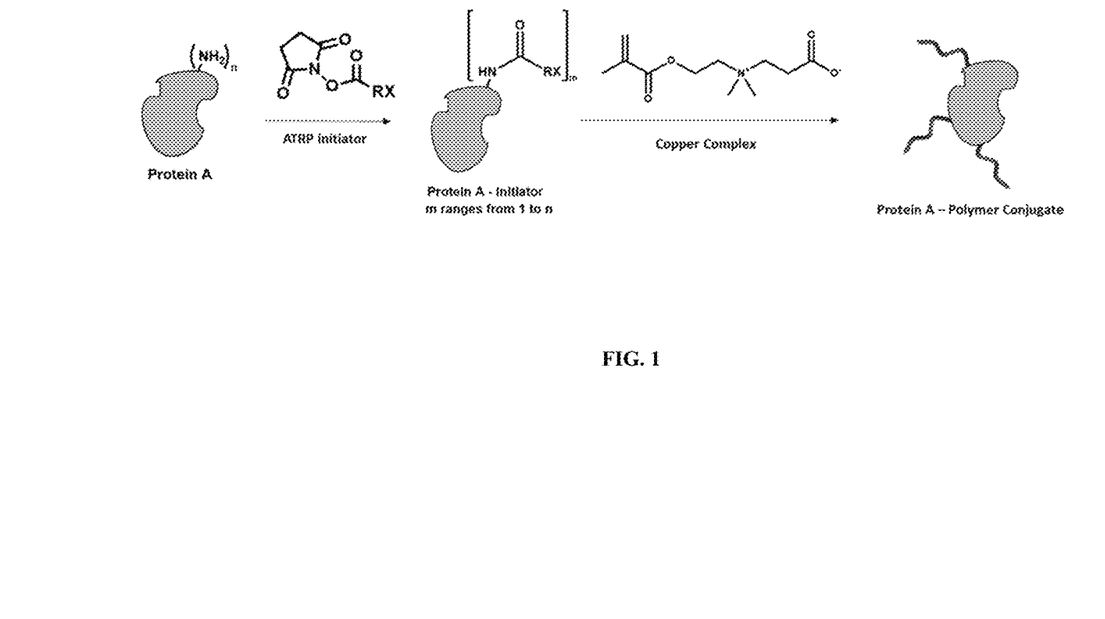
FIG. 1 is a diagram showing atom transfer radical polymerization (ATRP) on a protein.

To grow polymers from the surface of antibody binding protein A, polymerization initiating groups are attached covalently to the lysine residues via activated ester chemistry (FIG. 1). The polymerization initiating group is alkyl halide that undergoes homolytic cleavage and forms a radical upon reaction with a transition metal complex such as copper (I) bromide/Tris(2-pyridylmethyl)amine (TPMA). Activated ester labelled alkyl halide ratio to the protein, protein concentration, buffer pH and type is varied to identify labelling conditions when protein A retains its antibody binding capacity. Staphylococcal Protein A has 52 lysine residues that can be potentially modified. Labelling efficiency is analyzed by fluorescamine assay and confirmed by mass spectrometry. Antibody binding activity is evaluated by gel permeation chromatography.

Example 2

Figure 2:
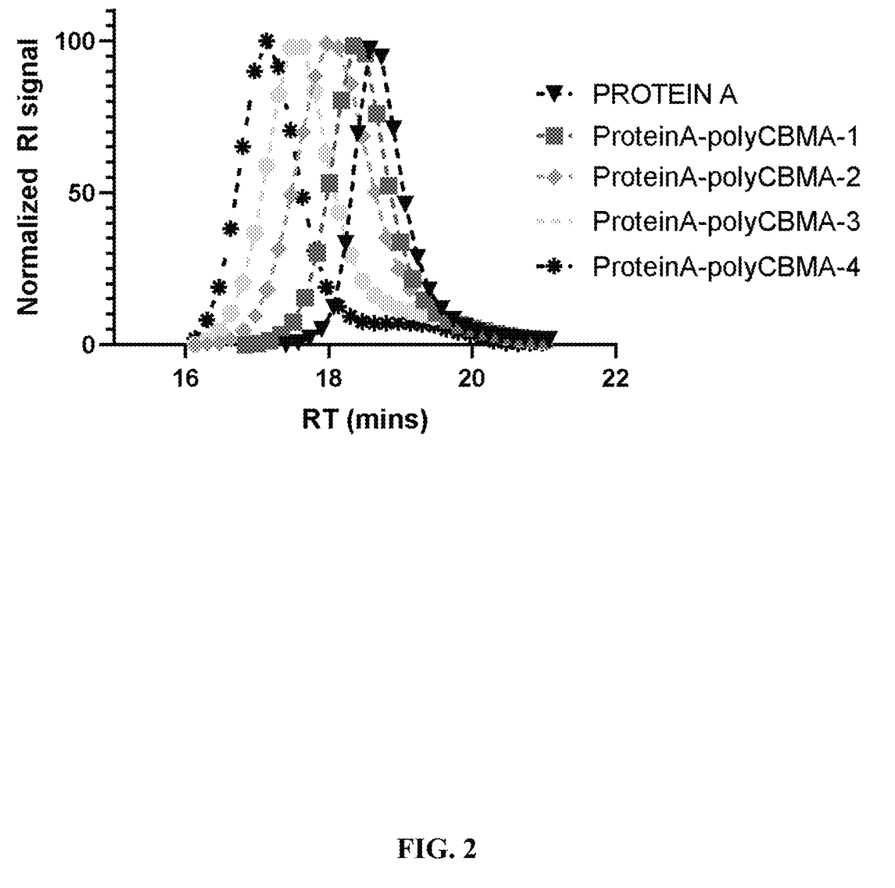
FIG. 2 is a composite chromatogram of protein (Protein A) and protein-based affinity ligands (Protein A-polyCBMA-#) characterized by gel permeation chromatography.

The polymerization initiator labelled protein A with retained activity to bind an antibody is further mixed with ATRP catalyst and a monomer (FIG. 1). Polymerization time, monomer concentration, and catalyst type are varied to produce protein-polymer conjugates of varied molecular weight. The monomer used is carboxybetaine methacrylate (CBMA) due to its high solubility in concentrated salt solutions. The conjugates were characterized using gel permeation chromatography (FIG. 2). Antibody binding activity of protein A is evaluated by gel permeation chromatography and gel electrophoresis.

Example 3

Figure 3:
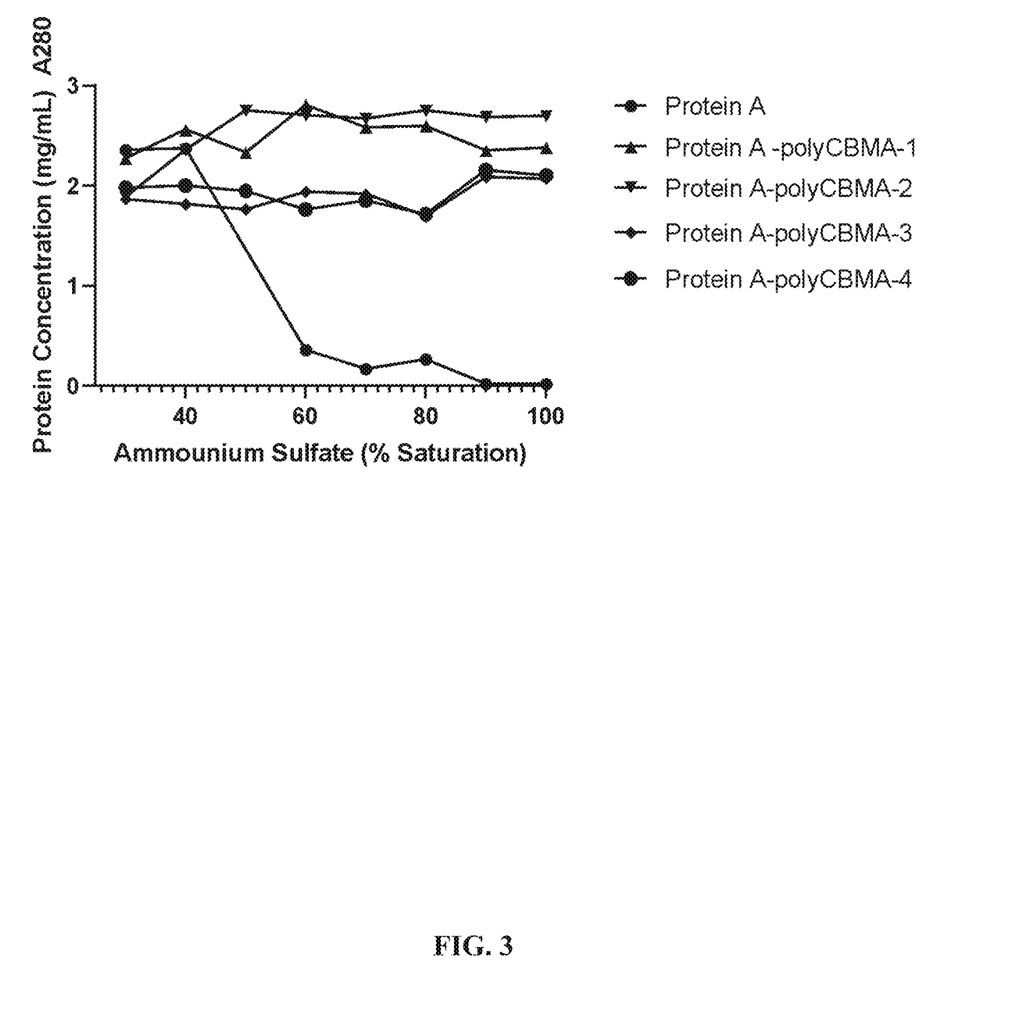
FIG. 3 is a graph of protein (Protein A) and protein-based affinity ligands (Protein A-polyCBMA-#) retention of solubility over increasing ammonium sulfate saturation in solution.

The solubility of the Protein A-polyCBMA conjugates in ammonium sulfate solutions with varied saturation (up to 100%) is evaluated by incubation at 4 and 30° C. for 10 min, followed by centrifugation. The protein concentration is evaluated in the supernatant by measurement of absorbance at 280 nm (FIG. 3). Protein-polymer size is evaluated by dynamic light scattering to determine hydrodynamic radius in ammonium sulfate solutions. Protein A-polyCBMA conjugates stay soluble in ammonium sulfate solutions even at 100% saturation (equivalent to 4.1M solution).

Example 4

Figure 4:
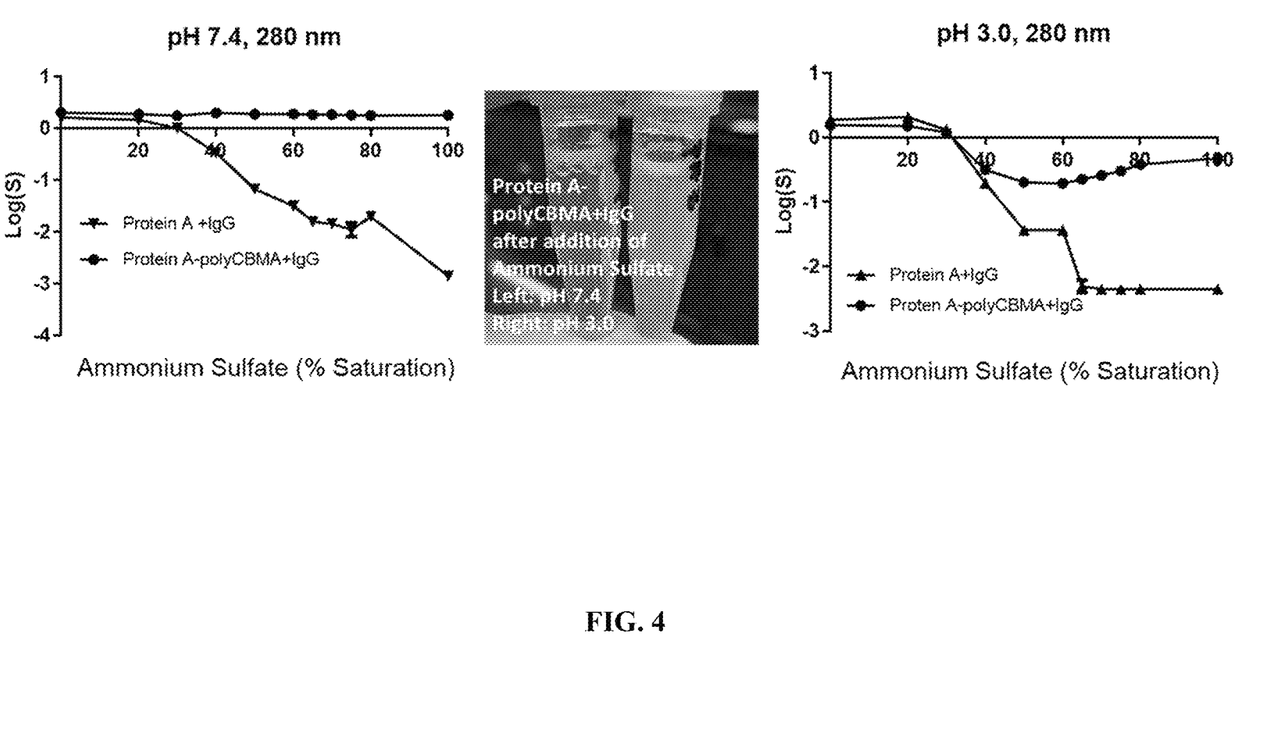
FIG. 4 is a composite figure for comparison of protein (Protein A) bound to antibody (IgG) and protein-based affinity ligands (Protein A-polyCBMA-#) bound to antibody (IgG) retention of solubility over increasing ammonium sulfate saturation in solution at neutral pH and the dissociation pH. Also included in the composite figure is a representative photograph of protein-based affinity ligand bound to antibody solution turbidity at the same ammonium sulfate saturation at neutral pH and the dissociation pH.
Figure 5:
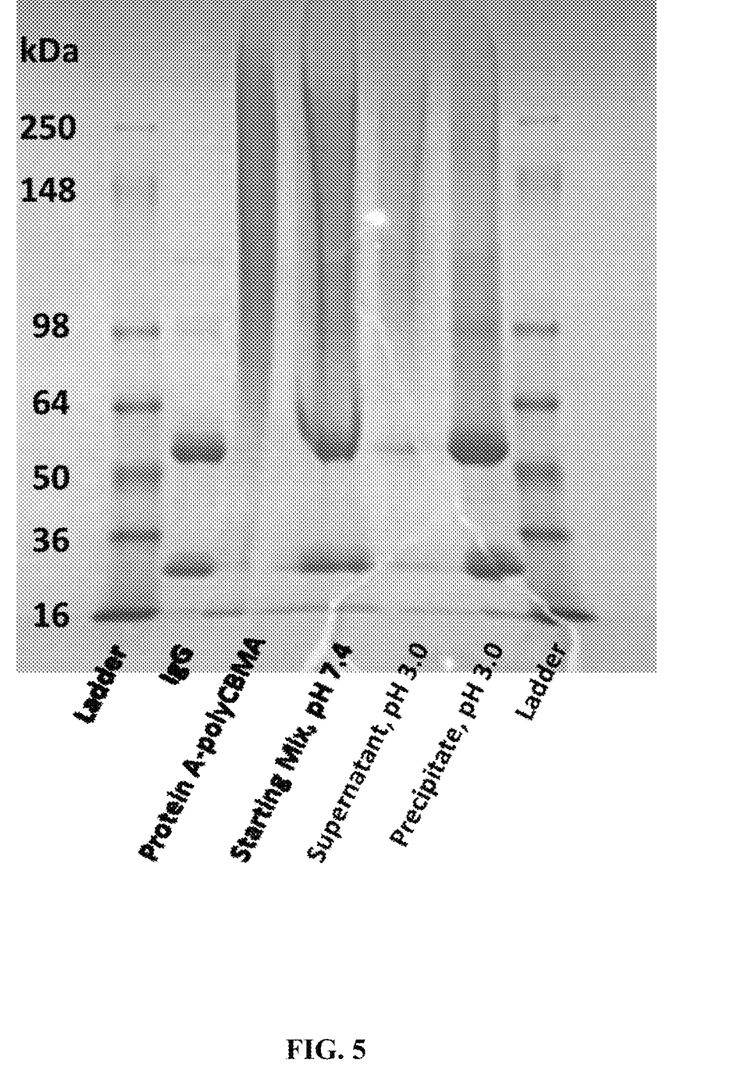
FIG. 5 is a photograph of the gel electrophoresis showing antibody (IgG), protein-based affinity ligand (Protein A-polyCBMA), protein-based affinity ligand bound to antibody at neutral pH (Starting Mix), the soluble portion of protein-based affinity ligand bound to antibody at the dissociation pH (Supernatant), and the reconstituted insoluble portion of protein-based affinity ligand bound to antibody at the dissociation pH (Precipitate).

Antibody is mixed with Protein A-polyCBMA at neutral pH (7.4) (FIG. 4). Ammonium sulfate is further added to the concentrations up to 100% saturation. At every additional 10% of ammonium sulfate, the solution is incubated for 10 min at 4 and 30° C., centrifuged, and the supernatant is analyzed for the residual protein concentration. Protein A-polyCBMA bound to the antibody stays soluble. Antibody bound to unmodified Protein A precipitates at concentrations above 40%. When antibody is mixed with Protein A-polyCBMA at acidic pH (3) and ammonium sulfate is added up to 100% saturation, then antibody precipitates at concentrations above 40% saturation while Protein A-pCBMA stays soluble. Gel electrophoresis analysis is used to show that under acidic pH only antibody is present in the precipitate, and only Protein A-pCBMA conjugate is present in the soluble fraction (FIG. 5).

Example 5

Figure 6:
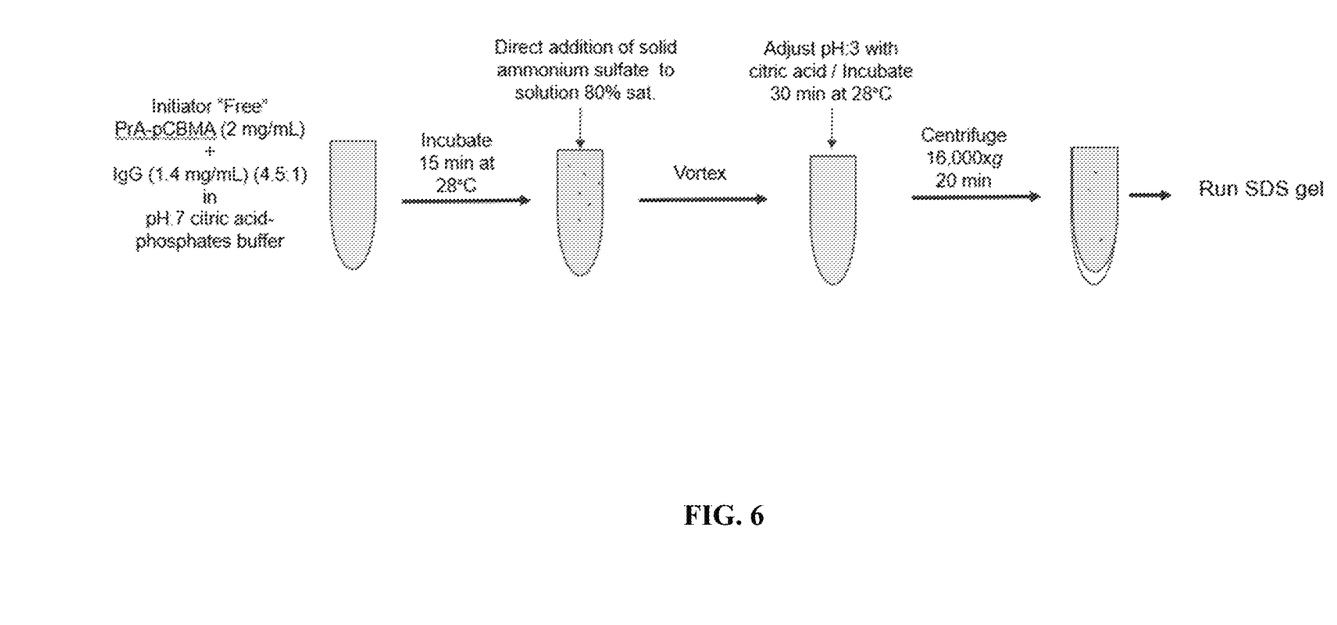
FIG. 6 is a diagram showing the method described herein in which protein-based affinity ligands covalently modified with a polymer bind to antibodies and remain soluble in solutions containing high concentrations of ammonium sulfate under neutral pH, while antibody disassociates and precipitates from the conjugate under acidic pH.
Figure 7:
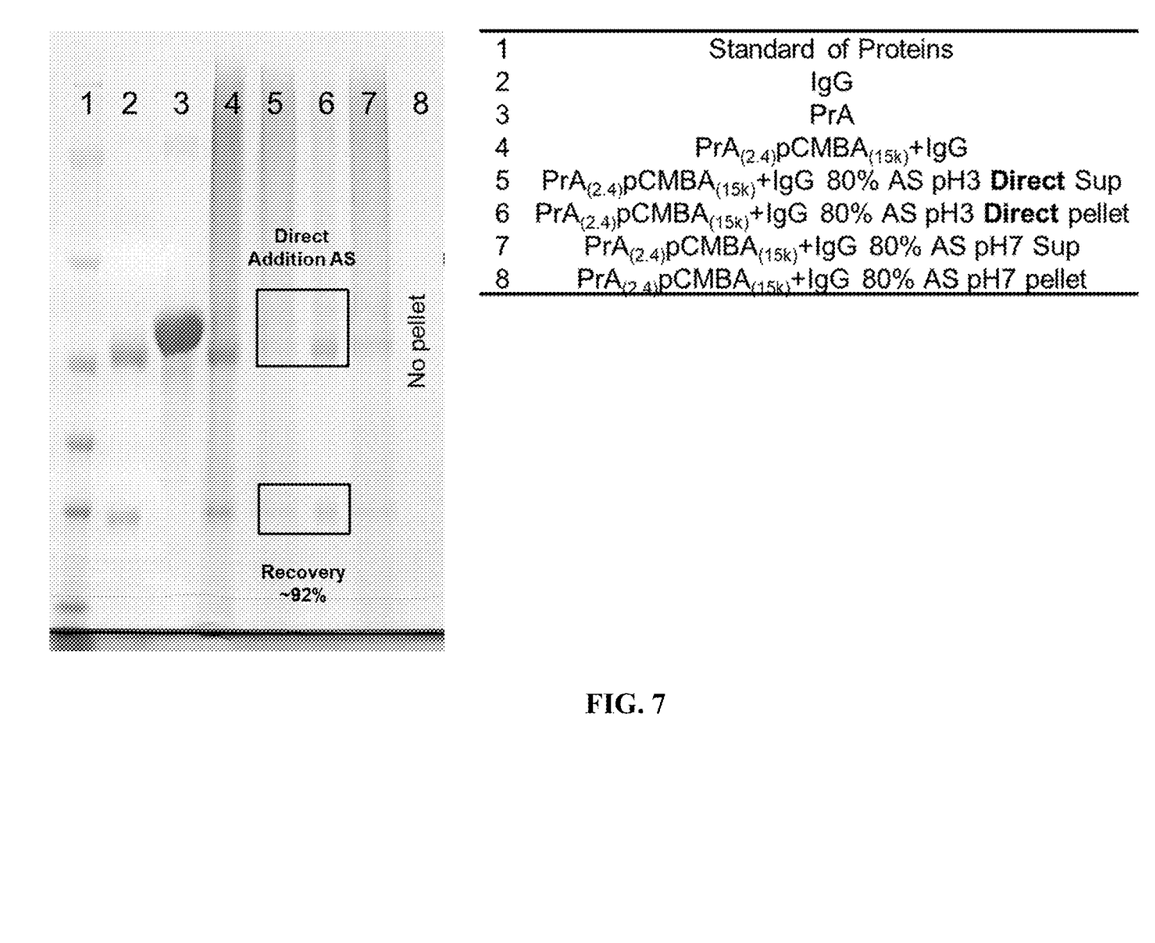
FIG. 7 is a photograph of the gel electrophoresis showing antibody (IgG), Protein A, protein-based affinity ligand conjugate (Protein A-polyCBMA) complexed with an antibody, supernatant of Protein A-polyCBMA mixture with antibody at pH=3 and ammonium sulfate at 80% saturation, precipitate of Protein A-polyCBMA mixture with antibody at pH=3 and ammonium sulfate at 80% saturation, supernatant of Protein A-polyCBMA mixture with antibody at pH=7 and ammonium sulfate at 80% saturation, and precipitate of Protein A-polyCBMA mixture with antibody at pH=7 and ammonium sulfate at 80%.

Antibody is mixed with Protein A-polyCBMA at neutral pH (7.4) at a ratio of 1:4.5 (FIG. 6). Ammonium sulfate is added until 80% saturation at 28° C. The bound antibody is separated from the protein A-polyCBMA conjugate by changing the pH to cause dissociation. The pH of the solution is reduced to 3. Disassociated antibody precipitates in ammonium sulfate solution. The solution is incubated for 0.5 h and centrifuged. The supernatant and precipitate are analyzed by gel electrophoresis (FIG. 7). Gel electrophoresis characterization shows that antibody is predominantly present in the precipitate, while Protein A-pCBMA conjugate stays in supernatant, indicating successful antibody separation.

Example 6

Figure 8:
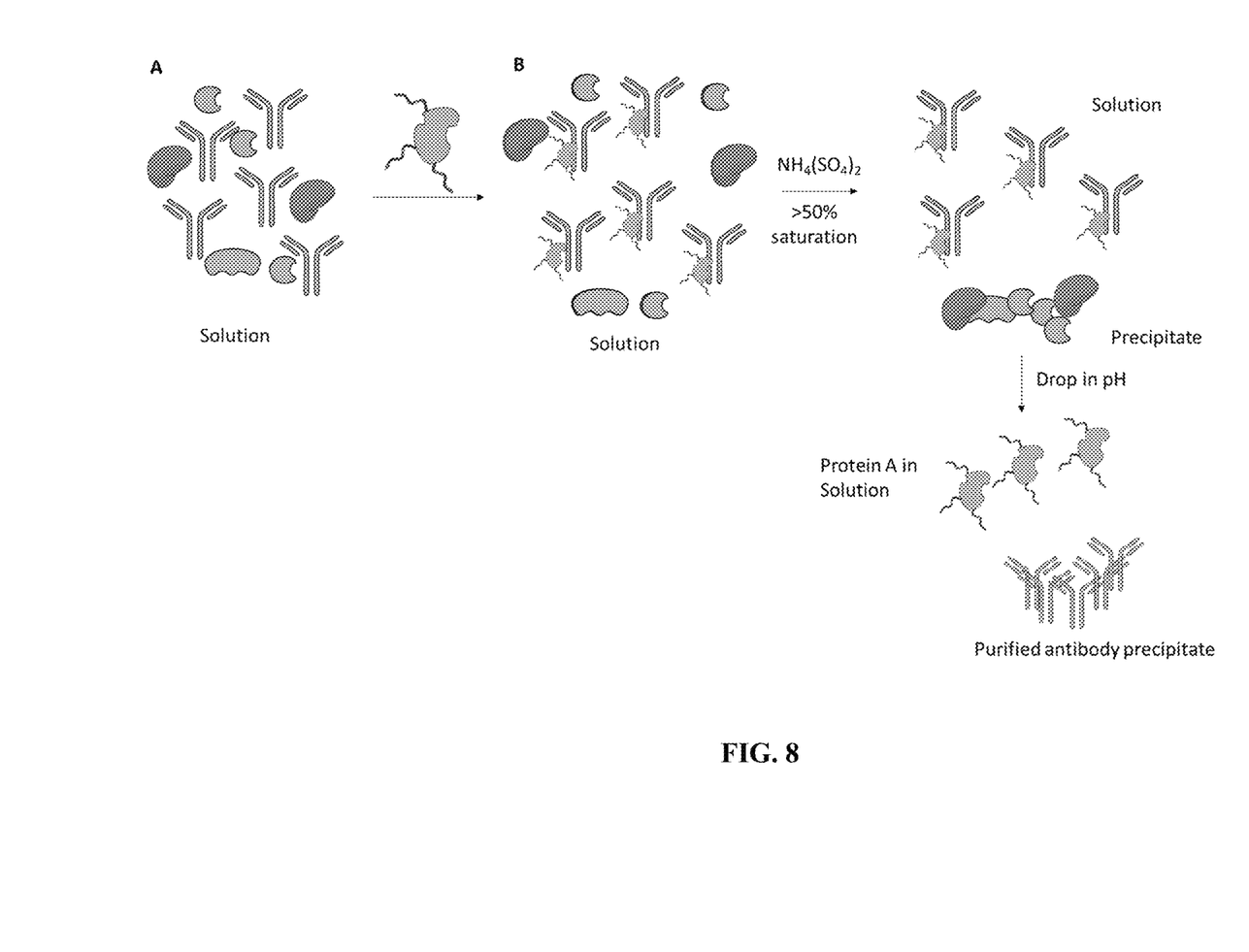
FIG. 8 is a diagram showing methods in which antibody-based affinity ligands bind to target proteins and remain soluble in solutions containing high concentrations of ammonium sulfate, while non-bound proteins are precipitated out of the solution.

In another example Protein A-polyCBMA conjugate will be used to purify the monoclonal antibody (mAb) from the host cell proteins in crude production media (FIG. 8). Crude monoclonal antibody solutions in production media will be mixed with Protein A-polyCBMA conjugate using 1 to 10 equivalents of conjugate to mAb. Ammonium sulfate will be added to the mixture (as a solid or a concentrated solution of 95%) to reach up to 85% saturation. The antibody-Protein A-polyCBMA conjugate associated complex will be recovered by decanting the supernatant following centrifugation, while the majority of host cell proteins will be removed as a white precipitate. To achieve dissolution of the antibody-Protein A-polyCBMA conjugate associated complex the pH will be slowly lowered to pH 2, initiating precipitation of mAb as the antibody-Protein A-polyCBMA conjugate complex begins to dissociate. Following complete dissociation of the antibody-Protein A-polyCBMA conjugate associated complex the pure mAb will be recovered by centrifugation and the precipitate will be dissolved in appropriate buffer at neutral pH. The recovery yield of mAb will be determined by measurement of absorbance at 280 nm. The purity of the purified antibody will be analyzed by gel electrophoresis.

Example 7

The polymerization initiator labeled protein A initiator with retained activity to bind an antibody will be further mixed with ATRP catalyst and a monomer. Polymerization time, monomers composition and concentration, catalyst type will be varied to produce protein-polymer conjugates of varied molecular weight. Monomer used will be carboxybetaine methacrylate in combination with sulfobetaine methacrylate due to their high solubility in concentrated salt solutions. Additionally, sulfobetaine methacrylate inclusion introduces T-sensitive precipitation upon cooling, conferring a property useful for protein A recycling.

Protein A-polyCBMA-r-SBMA conjugate will be mixed with human immunoglobulin at ratios 1:2, 1:1, and 2:1 in neutral pH buffer. The solution will be chilled until the protein A-polymer or complex with antibody will be precipitated out of solution. This method simplifies recycling and recovery of protein A-polyCBMA-r-SBMA conjugate. The supernatant will be removed and the precipitated protein A-polymer or complex with antibody will be resuspended. Upon decrease of pH the antibody will dissociate from the protein A-polyCBMA-rSBMA conjugate and precipitate because it is not attached to the solubility-enabling polymer conjugate anymore. Protein A-polyCBMA-r-SBMA conjugate will be subjected to buffer exchange into neutral pH buffer such as PBS, concentrated and utilized again for affinity dissolution-based antibody purification.

Example 8

The polymerization initiator labelled protein A initiator with retained activity to bind an antibody is further mixed with ATRP catalyst and a monomer. Polymerization time, monomer and concentration, and catalyst type are varied to produce protein-polymer conjugates of varied molecular weight. Monomer used is 2-methacryloyloxyethyl phosphorylcholine (PCMA) due to its high solubility in concentrated salt solutions.

Protein A-polyPCMA conjugate is mixed with human immunoglobulin at ratios 1:2, 1:1, and 2:1 in neutral pH buffer. Under ideal antibody binding conditions, the ammonium sulfate solutions is added step-wise up to 100% saturation. At every additional 10% of ammonium sulfate, the solution is incubated for 10 min at 4 and 30° C., centrifuged, and the supernatant is analyzed for the residual protein concentration. Most proteins precipitate at about 50% saturation of ammonium sulfate. The precipitation of the antibody is not observed at ammonium sulfate saturation above 50% because it is bound to protein A-polyPCMA conjugate. At saturations above 50% the solution is acidified until pH enters the range of 5 to 3. At each pH change of 0.5 the solution is incubated for 10 min, centrifuged, and residual protein concentration is analyzed in the supernatant and in the pellet if one is formed. Upon decrease of pH the antibody dissociates from the protein A-polyPCMA conjugate and precipitates because it is not attached to the solubility-enabling polymer conjugate anymore. The supernatant is removed and the precipitated antibody is resuspended. Protein A-polyPCMA conjugate is subjected to buffer exchange into neutral pH buffer such as PBS, concentrated, and utilized again for affinity dissolution-based antibody purification.

Example 9

In another example a polymer-modified antibody or antibody fragment will be designed to be used to recover a targeted protein of interest from cell extracts. Antibody which can recognize and bind to a protein of interest is modified with the ATRP initiator and subjected to polymerization in the presence of carboxybetaine methacrylate. In this example polyCBMA will be grown from the anti-green fluorescent protein (GFP) antibody. The ability of the antibody-polyCBMA conjugate to bind its antigen (GFP) will be analyzed by gel permeation chromatography. Antibody-polyCBMA conjugate will be mixed with its antigen, GFP, at ratios 1:2, 1:1, and 2:1 in neutral pH buffer in the presence of non-binding protein such as bovine serum albumin. Their binding will be evaluated in buffer utilizing gel permeation chromatography. Under ideal antibody binding conditions, the ammonium sulfate solution will be added step-wise up to 100% saturation. At every additional 10% of ammonium sulfate, the solution will be incubated for 10 min at 4 and 30° C., centrifuged, and the supernatant will be analyzed for residual protein concentration. Most proteins precipitate at about 50% saturation of ammonium sulfate. The precipitation of the protein of interest will not be observed at ammonium sulfate saturation above 50% because it is bound to antibody-polyCBMA conjugate. At saturations above 50% the solution will be acidified to a pH range of 5 to 3. At each pH change of 0.5 the solution will be incubated for 10 min, centrifuged, and residual protein concentration will be analyzed in the supernatant and in the pellet if one is formed. Upon decrease of pH the protein of interest will dissociate from the antibody-polyCBMA conjugate and precipitate because it is not attached to the solubility-enabling polymer conjugate anymore. Antibody-polyCBMA conjugate will be subjected to buffer exchange into neutral pH buffer such as phosphate buffered saline (PBS), 4-(2-hydroxyethyl)-1-piperazineethanesulfonic acid (HEPES), borate buffered saline (BBS), or 2-(N-morpholino)ethanesulfonic acid (MES), concentrated, and utilized again for affinity dissolution-based antibody purification.

The invention claimed is:

1. A method for purifying proteins comprising:
   adding a protein-based affinity ligand comprising a protein covalently attached to a betaine osmolyte to a solution containing a target protein;
   adding a precipitant to the solution;
   recovering a supernatant from the solution; and
   extracting the target protein from the protein-based affinity ligand.

2. The method of claim 1, further comprising removing precipitated proteins precipitated by the precipitant from the solution.

3. The method of claim 1, wherein the precipitant is selected from the group consisting of chloride salts, sulfate salts, phosphate salts, acetate salts, citrate salts, sodium chloride, ammonium sulfate, ammonium chloride, potassium chloride, sodium acetate, and combinations thereof.

4. The method of claim 1, wherein the precipitant is a salt solution having saturation level of greater than about 40%.

5. The method of claim 1, wherein extracting the target protein comprises decreasing the pH of the solution containing complexes of the protein-based affinity ligand and the target protein.

6. The method of claim 5, wherein the pH of the solution is lowered to a pH of about 5 to about 3.

7. The method of claim 1, wherein the protein is selected from the group consisting of antibodies, protein A, protein G, protein A/G, protein L, and jacalin.

8. The method of claim 1, wherein the betaine osmolyte is selected from the group consisting of sulfobetaine methacrylate (SBMA), sulfobetaine acrylate, sulfobetaine acrylamide, sulfobetaine methacrylamide, carboxybetaine methacrylate (CBMA), carboxybetaine acrylate, carboxybetaine acrylamide, carboxybetaine methacrylamide, phosphorylcholine methacrylate (PCMA), phosphorylcholine acrylate, phosphorylcholine acrylamide, phosphorylcholine methacrylamide, and combinations thereof.

9. The method of claim 1, wherein the betaine osmolyte is selected from the group consisting of poly(carboxy betaine methacrylate) (polyCBMA), poly(carboxybetaine acrylate), poly(carboxybetaine acrylamide), poly(carboxybetaine methacrylamide), poly(sulfobetaine methacrylate) (polySBMA), poly(sulfobetaine acrylate), poly(sulfobetaine acrylamide), poly(sulfobetaine methacrylamide), poly(phosphorylcholine methacrylate) (polyPCMA), poly(phosphorylcholine acrylate), poly(phosphorylcholine acrylamide), and poly(phosphorylcholine methacrylamide).

10. A method for purifying a protein comprising:
adding a protein-based affinity ligand comprising a protein and a covalently attached to a betaine osmolyte to a solution containing a target protein;
reducing the temperature of the solution;
concentrating a precipitated protein-based affinity ligand-target protein complexes from the solution; and
removing a supernatant from the solution.

11. The method of claim 10, further comprising resuspending the precipitated protein-based affinity ligand-target protein complexes in a solution and extracting the target protein from the protein-based affinity ligand.

12. The method of claim 11, wherein extracting comprises decreasing the pH of the solution containing the protein-based affinity ligand-target protein complexes.

13. The method of claim 12, wherein the pH of the solution is lowered to a pH of about 5 to about 3.

14. The method of claim 10, wherein the protein is selected from the group consisting of antibodies, protein A, protein G, protein A/G, protein L, and jacalin.

15. The method of claim 10, wherein the betaine osmolyte is selected from the group consisting of sulfobetaine methacrylate (SBMA), sulfobetaine acrylate, sulfobetaine acrylamide, sulfobetaine methacrylamide, carboxybetaine methacrylate (CBMA), carboxybetaine acrylate, carboxybetaine acrylamide, carboxybetaine methacrylamide, phosphorylcholine 4 methacrylate (PCMA), phosphorylcholine acrylate, phosphorylcholine acrylamide, phosphorylcholine methacrylamide, and combinations thereof.

16. The method of claim 10, wherein the betaine osmolyte is selected from the group of consisting poly(carboxy betaine methacrylate) (polyCBMA), poly(carboxybetaine acrylate), poly(carboxybetaine acrylamide), poly(carboxybetaine methacrylamide), poly(sulfobetaine methacrylate) (polySBMA), poly(sulfobetaine acrylate), poly(sulfobetaine acrylamide), poly(sulfobetaine methacrylamide), poly(phosphorylcholine methacrylate) (polyPCMA), poly(phosphorylcholine acrylate), poly(phosphorylcholine acrylamide), and poly(phosphorylcholine methacrylamide).

* * * * *